United States Patent
Knobloch

(10) Patent No.: US 9,249,786 B1
(45) Date of Patent: *Feb. 2, 2016

(54) GEOTHERMAL RECOVERY METHOD AND SYSTEM

(71) Applicant: Charles Saron Knobloch, Katy, TX (US)

(72) Inventor: Charles Saron Knobloch, Katy, TX (US)

(*) Notice: Subject to any disclaimer, the term of this patent is extended or adjusted under 35 U.S.C. 154(b) by 226 days.

This patent is subject to a terminal disclaimer.

(21) Appl. No.: 13/769,796

(22) Filed: Feb. 18, 2013

Related U.S. Application Data

(63) Continuation of application No. 12/632,794, filed on Dec. 7, 2009, now Pat. No. 8,398,862.

(60) Provisional application No. 61/120,079, filed on Dec. 5, 2008.

(51) Int. Cl.
*F03G 7/00* (2006.01)
*B01D 1/00* (2006.01)
(Continued)

(52) U.S. Cl.
CPC .. *F03G 7/00* (2013.01); *B01D 1/00* (2013.01); *C07C 7/04* (2013.01); *C07C 7/10* (2013.01); *F01K 3/188* (2013.01); *F01K 27/00* (2013.01); *Y02E 10/10* (2013.01); *Y02E 20/00* (2013.01)

(58) Field of Classification Search
CPC ...... B01D 1/00; B01D 1/0064; B01D 1/0011; B01D 1/0041; B01D 1/0047; B01D 1/0058; B01D 17/00; B01D 17/12; Y02E 10/00; Y02E 10/10; Y02E 10/16; Y02E 10/40; Y02E 10/46; Y02E 20/00; Y02E 20/12; Y02E 20/14; B01J 10/00; B01J 14/00; B01J 7/00; F01K 25/00; F01K 25/10; F01K 25/14; F01K 25/065; F01K 25/103; F01K 27/00; F01K 27/02; F01K 3/18; F01K 3/24; F01K 3/188; C07C 7/00; C07C 7/10; C07C 7/11; C07C 7/04; F03G 7/00
USPC ............... 166/244.1, 272.1, 272.6, 305.1; 60/39.12, 780, 39.01, 39.461, 772, 60/641.1, 641.2, 641.3; 423/580.1; 159/47.1, 47.3; 429/400, 428; 210/600, 210/652, 702, 737, 747.1, 747.7, 758, 774, 210/806; 203/10, 11, 21, 31; 290/54
See application file for complete search history.

(56) References Cited

U.S. PATENT DOCUMENTS 4,031,956 A * 6/1977 Terry ............................ 166/261
4,052,858 A * 10/1977 Jeppson ......................... 60/648
(Continued)

OTHER PUBLICATIONS

Publication: "Current status of hydrogen energy", M. Momirlan et al, 'Renewable and Sustainable Energy Reviews', vol. 6, 2002, pp. 141-179.*

*Primary Examiner* — Joseph Drodge

(57) ABSTRACT

A method for extracting energy from hydrocarbons located in a geologic reservoir is presented, including the steps of: oxidizing the hydrocarbons; extracting heat generated from oxidizing the hydrocarbons, relocating oxidized gases away from the oxidizing hydrocarbons; and replenishing oxygen towards the oxidizing hydrocarbons. The extraction of heat further includes: evaporating a liquid; transferring the evaporated liquid to the surface; and recovering low-NaCl, low-precipitate water from the evaporated liquid. The replenishing of oxygen towards the oxidizing hydrocarbons further includes: generating oxygen from water; and transferring the generated oxygen toward the oxidizing hydrocarbons; and combining hydrogen derived from the generating step with surface oxygen, whereby heat and low-precipitate, pure water is produced.

19 Claims, 4 Drawing Sheets

(51) Int. Cl.
*C07C 7/10* (2006.01)
*C07C 7/04* (2006.01)
*F01K 27/00* (2006.01)
*F01K 3/18* (2006.01)

(56) References Cited

U.S. PATENT DOCUMENTS

| | | | | |
|---|---|---|---|---|
| 6,216,463 B1 * | 4/2001 | Stewart | ............ | 60/641.2 |
| 6,277,338 B1 * | 8/2001 | Agee et al. | ............ | 422/618 |
| 6,596,780 B2 * | 7/2003 | Jahnke et al. | ............ | 518/700 |
| 6,820,689 B2 * | 11/2004 | Sarada | ............ | 166/266 |
| 7,828,385 B2 * | 11/2010 | Reubeuze | ............ | 297/366 |
| 7,828,938 B2 * | 11/2010 | Bowman | ............ | 202/176 |
| 7,866,385 B2 * | 1/2011 | Lambirth | ............ | 166/256 |
| 7,922,873 B2 * | 4/2011 | St. Germain et al. | ............ | 202/155 |
| 8,327,932 B2 * | 12/2012 | Karanikas et al. | ............ | 166/251.1 |
| 8,398,862 B1 * | 3/2013 | Knobloch | ............ | 210/747.7 |
| 8,826,638 B1 * | 9/2014 | Gurin | ............ | 60/39.6 |
| 2006/0053791 A1 * | 3/2006 | Prentice, III | ............ | 60/645 |
| 2006/0096298 A1 * | 5/2006 | Barnicki et al. | ............ | 60/781 |
| 2006/0137349 A1 * | 6/2006 | Pflanz | ............ | 60/641.2 |
| 2008/0142217 A1 * | 6/2008 | Pieterson et al. | ............ | 166/272.6 |
| 2010/0022669 A1 * | 1/2010 | Cohn et al. | ............ | 518/703 |
| 2010/0077752 A1 * | 4/2010 | Papile | ............ | 60/641.8 |

* cited by examiner

GEOTHERMAL RECOVERY METHOD AND SYSTEM

STATEMENT OF RELATED CASES

This application is a continuation of U.S. application Ser. No. 12/632,794 of filing date 7 Dec. 2009. U.S. application Ser. No. 12/632,794 of filing date 7 Dec. 2009 claims the benefit of U.S. Provisional Application 61/120,079 of filing date 5 Dec. 2008.

FIELD OF THE INVENTION

This invention relates to geothermal recovery by combustion of in-place hydrocarbons. In a particular example, the in-place hydrocarbons are an oil and/or gas reservoir (oil field) and the combustion takes place in a well that penetrates the geologic reservoir.

DESCRIPTION SUMMARY OF THE INVENTION

In a first example, a method for extracting energy from hydrocarbons located in a geologic reservoir is presented, the method including the steps of: oxidizing the hydrocarbons; extracting heat generated from oxidizing the hydrocarbons; relocating oxidized gases away from the oxidizing hydrocarbons; and replenishing oxygen towards the oxidizing hydrocarbons.

In another example, the extracting step includes introducing a liquid towards the oxidizing hydrocarbons. In another example, the liquid is operable to evaporate. In another example, the liquid includes water. In another example, the liquid is introduced using a heat exchanger. In another example, the liquid is introduced through closed pipe. In another example, the water is sourced from a geologic formation.

In another example, the liquid is introduced from the surface. In another example, the liquid is sourced proximate from the geologic reservoir. In another example, the liquid is circulated in a substantially closed loop. In another example, the liquid is replenished with water sourced from a geologic formation.

In another example, the method further comprises the step of shunting precipitates produced from the extracting step.

In another example, the extracting step includes the step of evaporating a liquid. In another example, the evaporating step further includes the step of removing the evaporating liquid. In another example, the evaporating step further includes the step of recovering low-NaCl, low-precipitate water from the evaporating liquid.

In another example, the replenishing step includes the steps of: generating oxygen from water; and transferring the generated oxygen toward the oxidizing hydrocarbons.

In another example, the process further includes combining hydrogen derived from the generating step with surface oxygen, whereby heat and low-precipitate, pure water is produced.

In another example, the relocating step includes relocating the oxidized gases into a lower pressure formation. In another example, the relocating step includes relocating the oxidized gases into another location into a geologic reservoir. In another example, the relocating step includes relocating the oxidized gases into another location into a geologic reservoir, whereby the gases provide pressure for secondary recovery operations. In another example, the relocating step includes relocating the oxidized gases into a lower point in the geologic reservoir containing hydrocarbons, whereby additional pressure is introduced for enhanced recovery operations.

In another example, a method for extracting energy from hydrocarbons located in a geologic reservoir is presented, including the steps of: oxidizing the hydrocarbons; extracting heat generated from oxidizing the hydrocarbons, further comprising: evaporating a liquid; transferring the evaporated liquid to the surface; and recovering low-NaCl, low-precipitate water from the evaporated liquid; relocating oxidized gases away from the oxidizing hydrocarbons; and replenishing oxygen towards the oxidizing hydrocarbons, further comprising: generating oxygen from water; and transferring the generated oxygen toward the oxidizing hydrocarbons; and combining hydrogen derived from the generating step with surface oxygen, whereby heat and low-precipitate, pure water is produced.

In an example, in-situ hydrocarbons are oxidized. The generated heat from the oxidizing hydrocarbons is extracted. The oxidized gases are relocated away from the oxidizing hydrocarbons. The oxygen is replenished towards the oxidizing hydrocarbons.

In one example, the extracting step includes introducing water, in one of a choice of various manners, and shunting the precipitates.

In one example, the replenishing step includes generating oxygen from water and transferring to the oxidizing hydrocarbons. In one example, generated hydrogen is combined with surface oxygen to produce heat and low precipitate (nearly pure) water.

In one example, the relocating step includes using a lower pressure formation. In another example, the relocating step includes steam injection at another location, such as at a lower point in the reservoir.

BRIEF DESCRIPTION OF THE DRAWINGS

Various aspects of the invention, including alternative embodiments and the various functionalities associated therewith, are disclosed with particularity in the attached drawing sheets, FIGS. 1-4.

DETAILED DESCRIPTION

Figure 1:
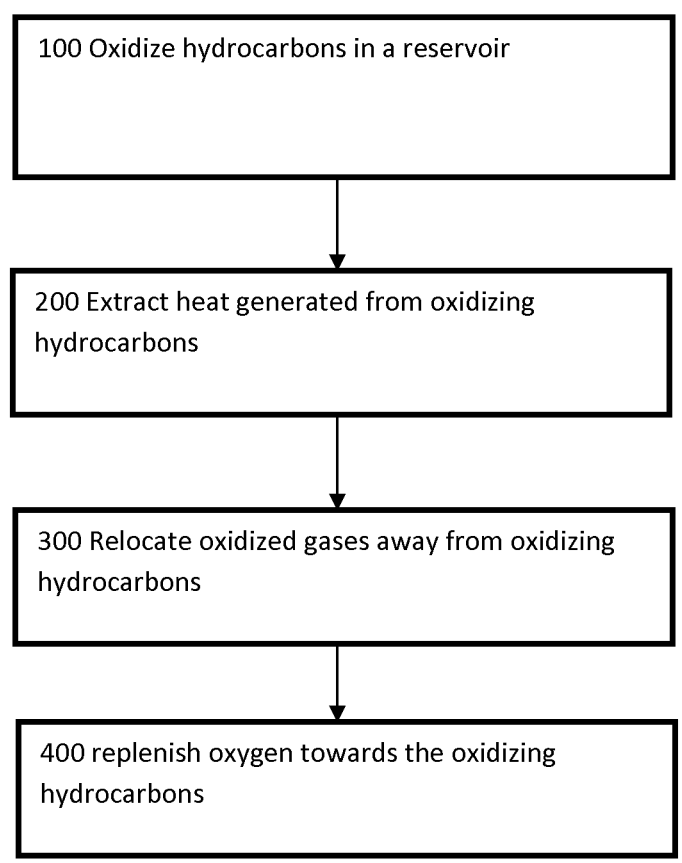
FIGS. 1-4 display flow charts of the method.

FIG. 1 illustrates a flow chart of the method. Hydrocarbons in a geologic reservoir are oxidized 100. Heat generated from oxidizing the hydrocarbons is extracted 200. Oxidized gases are relocated away from the oxidizing hydrocarbons 300. Oxygen is replenished towards the oxidizing hydrocarbons 400. In one example, these steps are performed through one or more boreholes that is/are in communication between the earth surface and the geologic reservoir.

Figure 2:
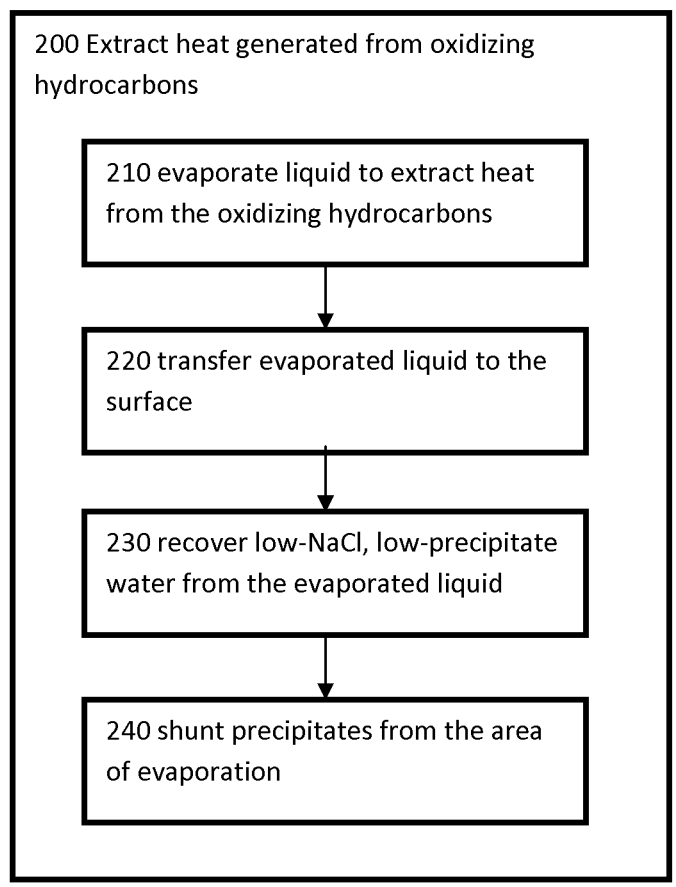

In one example, FIG. 2, heat extraction step 200 is further detailed in that a liquid is evaporated 210 and the evaporated liquid is transferred to the surface 220. In one example, the liquid is maintained by pressure in a liquid state for evaporation at the surface. In one example, low-NaCl, low-precipitate water from the evaporated liquid is recovered 230. In another example, precipitates produced by extraction step, for example, salt produced during evaporation, are shunted away from the area of evaporation 240.

Figure 3:
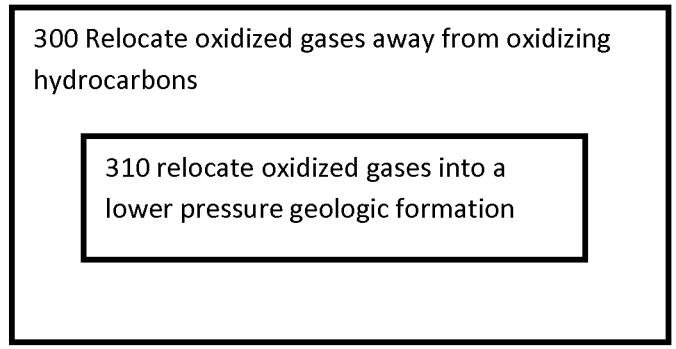

In one example, FIG. 3, the step of relocating oxidized gases 300 is further detailed in that the oxidized gases are relocated into a lower pressure geologic formation 310. It can be appreciated that in other examples, the oxidized gases are relocated into another location into a geologic reservoir, whereby the gases provide pressure for secondary recovery operations. In another example, the relocating step includes relocating the oxidized gases into a lower point in the geologic reservoir containing hydrocarbons, whereby additional pressure is introduced for enhanced recovery operations.

Figure 4:
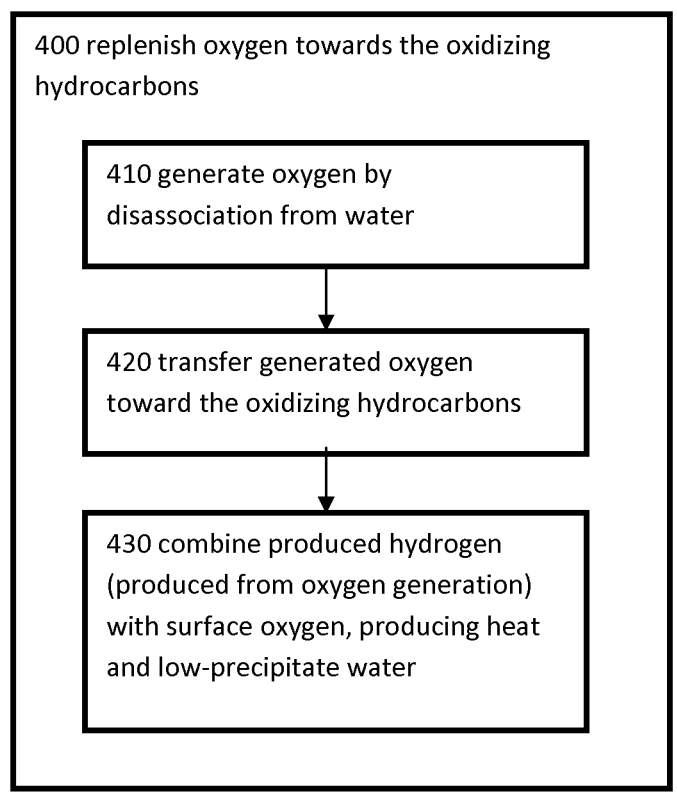

In one example, FIG. 4, the step of replenishing the oxygen 400 is further detailed in that oxygen is generated by disassociation from water 410. In one example, the generated oxygen is transferred toward the oxidizing hydrocarbons 420. In one example, the hydrogen produced from the oxygen generation step is combined with surface oxygen 430, producing heat and low-precipitate, pure water.

The foregoing description is intended primarily for illustrative purposes, and is not intended to include all possible aspects of the present invention. Moreover, while the invention has been shown and described with respect to a presently preferred examples, those of ordinary skill in the art will appreciate that the description, and various other modifications, omissions and additions, so long as in the general form and detail, may be made without departing from either the spirit or scope thereof.

The invention claimed is:

1. A method for extracting energy from hydrocarbons located in a geologic reservoir, the method comprising:
   oxidizing the hydrocarbons;
   extracting heat generated from oxidizing the hydrocarbons;
   relocating produced oxidized gases away from the oxidizing hydrocarbons; and
   replenishing oxygen towards the oxidizing hydrocarbons; and
   wherein the replenishing step comprises:
      generating oxygen from water; and
      transferring the generated oxygen towards the oxidizing hydrocarbons.

2. The method of claim 1 wherein the extracting step comprises introducing a liquid towards the oxidizing hydrocarbons.

3. The method of claim 2 wherein the liquid is evaporable.

4. The method of claim 2 wherein the liquid comprises water.

5. The method of claim 4 wherein the liquid comprising water is sourced from a geologic formation.

6. The method of claim 2 wherein the liquid is introduced using a heat exchanger.

7. The method of claim 2 wherein the liquid is introduced through a closed pipe.

8. The method of claim 2 wherein the liquid is introduced from the earth surface.

9. The method of claim 2 wherein the liquid is in a substantially closed loop.

10. The method of claim 2 wherein the liquid is replenished with water sourced from a geologic formation.

11. The method of claim 1 further comprising shunting precipitates produced from the extracting step.

12. The method of claim 1 wherein the extracting step comprises evaporating a liquid.

13. The method of claim 1 wherein the evaporating step comprises removing the evaporating liquid.

14. The method of claim 1 wherein the evaporating step comprises recovering low-NaCl, low-precipitate water from the evaporating liquid.

15. The method of claim 1 further comprises combining hydrogen derived from the generating step with surface oxygen, whereby heat and low-precipitate, pure water is produced.

16. The method of claim 1 wherein the relocating step comprises relocating the oxidized gases into a lower pressure geologic formation.

17. The method of claim 1 wherein the relocating step comprises relocating the oxidized gases into another location into a geologic reservoir.

18. The method of claim 1 wherein the relocating step comprises relocating the oxidized gases into another location into a geologic reservoir, whereby the gases provide pressure for secondary recovery operations.

19. The method of claim 1 wherein the relocating step comprises relocating the oxidized gases into a lower point in the geologic reservoir containing hydrocarbons, whereby additional pressure is introduced for enhanced recovery operations.

* * * * *